United States Patent [19]

Labeda et al.

[11] 4,407,946

[45] Oct. 4, 1983

[54] PROCESS FOR PRODUCING ANTIBIOTIC X-14868A

[75] Inventors: David P. Labeda, Monsey; John H. E. J. Martin, New City; Joseph J. Goodman, Spring Valley, all of N.Y.

[73] Assignee: American Cyanamid Company, Stamford, Conn.

[21] Appl. No.: 313,849

[22] Filed: Oct. 22, 1981

[51] Int. Cl.³ .......................... C12P 19/60; C12P 1/04; C12R 1/03; C12N 1/20
[52] U.S. Cl. ...................................... 435/75; 435/170; 435/825; 435/875; 435/253
[58] Field of Search ................. 435/825, 872, 75, 170, 435/253

[56] References Cited

U.S. PATENT DOCUMENTS 4,278,663  7/1981  Lui et al. ............................... 435/75

OTHER PUBLICATIONS

The American Type Culture Collection *Catalogue of Strains* I 1978, p. 24.
Gauze et al., Production of Madumycin, an antibacterial antibiotic, by Actinomadur Flava, *Chemical Abst.* vol. 82, 1975, p. 314.
Bergey, *Manual of Determinative Bacteriology*, Williams and Wilkins Co., 1974, Baltimore.

*Primary Examiner*—Thomas G. Wiseman
*Assistant Examiner*—K. McCowin
*Attorney, Agent, or Firm*—Jack W. Richards

[57] ABSTRACT

This invention relates to a novel process for the production of antibiotic X-14868A using the novel microorganism *Antinomadura yumaense* sp. nov.

5 Claims, No Drawings

PROCESS FOR PRODUCING ANTIBIOTIC X-14868A

BACKGROUND OF THE INVENTION

The present invention relates to a novel process for the production of the known antibiotic X-14868A using the novel microorganism *Actinomadura yumaense* sp. nov.

DESCRIPTION OF THE PRIOR ART

U.S. application Ser. No. 116,696 (filed Jan 30, 1981, now U.S. Pat. No. 4,278,663, assigned to Hoffman-LaRoche Inc. of Nutley, N.J.) discloses antibiotic X-14868A having the formula:

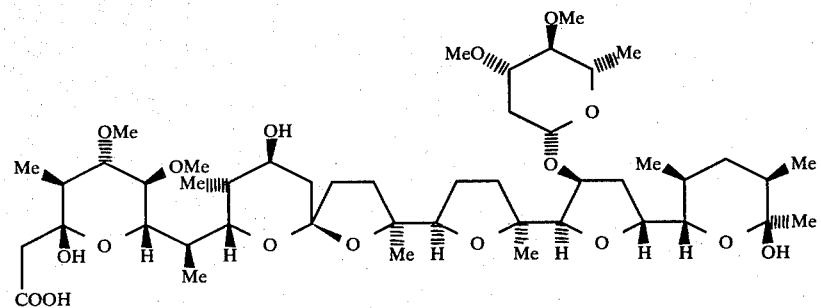

This antibiotic is described as being produced by the aerobic fermentation of a new species of Nocardia, designated Nocardia sp. X-14868, ATCC 31585, and is disclosed as being useful in the field of veterinary medicine for the treatment of coccidiosis, prevention and treatment of ketosis, improvement of feed utilization, and treatment and prevention of swine dysentery, as well as being useful as a bacteriocidal antiseptic.

BRIEF SUMMARY OF THE INVENTION

The present invention relates to the novel microorganism *Actinomadura yumaense* sp. nov.

This invention further concerns a novel process for the production of antibiotic X-14868A by fermentation under controlled conditions of the novel microorganism *Actinomadura yumaense* sp. nov.

More particularly, this invention relates to *Actinomadura yumaense* strain NRRL 12515 and to a process for producing antibiotic X-14868A by the fermentation under controlled conditions of this strain.

DETAILED DESCRIPTION OF THE INVENTION

In accordance with the present invention, there is provided a novel process for the production of the known antibiotic X-14868A by the cultivation under controlled conditions of the novel microorganism *Actinomadura yumaense* sp. nov.

A representative strain of this novel microorganism was isolated from a soil sample collected in Yuma County, Arizona and is maintained in the culture collection of the Lederle Laboratories Division, American Cyanamid Company, Pearl River, New York as culture number LL-C23024. A viable culture of this representative strain has been deposited with the Culture Collection Laboratory, Northern Regional Center, U.S. Department of Agriculture, Peoria, Illinois 61604, and has been added to its permanent collection under the accession number NRRL 12515. It is freely available to the public from this depository under its accession number NRRL 12515.

Taxonomic Characterization of NRRL 12515

The strain NRRL 12515 has been taxonomically characterized and identified as the type strain of a new species of the genus Actinomadura to be known as *Actinomadura yumaense* sp. nov.

Observations were made of the cultural, physiological and morphological features of representative strain NRRL 12515 using methods detailed by E. B. Shirling and D. Gottlieb, "Methods for characterization of Streptomyces species," Internat. J. Syst. Bacteriol. 16:313–340 (1966), and R. E. Gordon et al., "*Nocardia coeliaca, Nocardia autotrophica*, and the nocardin strain," Internat. J. Syst. Bacteriol. 24:54–63 (1974).

Media used in this study were selected from those recommended by T. G. Pridham et al., "A selection of media for maintenance and taxonomic study of Streptomycetes," Antibiotics Ann., pp. 947–953 (1956/1957); G. F. Gauze et al., "Problems in the classification of antagonistic actinomycetes," State Publishing House for Medical Literature, Medgiz, Moscow (1957); and R. E. Gordon et al., supra, for the taxonomic study of actinomycetes and soil bacteria. Chemical composition of the cell walls of the microorganism was determined using the method of H. A. Lechevalier et al., "Chemical composition as a criterion in the classification of actinomycetes," Adv. Appl. Microbiol. 14:47–72 (1971). Phospholipid patterns were determined using the method of M. P. Lechevalier et al., "Chemotaxonomy of aerobic actinomycetes: phospholipid composition," Biochem. Syst. Ecol. 5:249–260 (1977). Details are recorded in Tables I–VI, and a general description of the culture is given below. Underscored descriptive colors are taken from K. L. Kelly and D. B. Judd, "Color. Universal Language and Dictionary of Names," U.S. Nat. Bur. Stand., Spec. Publ. 440, Washington, D.C. (1976) and the accompanying Inter-Society Color Council, Natl. Bur. Stand. Centroid Color Charts.

The data observed for this novel species as represented by strain NRRL 12515 were compared with the data published for the known species of the genus Actinomadura [M. Goodfellow et al., "Numerical Taxonomy of Actinomadura and related actinomycetes," J. Gen. Microbiol. 112:95–111 (1979); L. H. Huang, "*Actinomadura macra* sp. nov., the producer of antibiotic CP-47,433 and CP-47,434," Internat. J. Syst. Bacteriol. 30:565–568 (1980); J. Meyer, "New species of the genus Actinomadura," Z. Allgem. Mikrobiol. 19:37–44 (1979); H. Nomura and Y. Ohara, "Distribution of actinomycetes in soil. XI. Some new species of the genus Actinomadura, Lechevalier, et al., "J. Ferment. Technol. 49:904–912 (1971); and T. P. Preobrazhenskaya et al., "Key for identification of the species of the genus Actinomadura," The Biology of Actinomycetes and Related Organisms 12:30–38 (1977)]. Culture NRRL 12515 bears a slight resemblance to *Actinomadura pelletieri*, but resembles no other described species and differs from *A. pelletieri* in a number of characteristics. Therefore, strain NRRL 12515 has been designated the type strain of a new species to be known as *Actinomadura yumaense*, sp. nov., named for the site of collection of the soil sample from which the type strain was isolated.

Micromorphology

Spores are formed in short spiral chains (maximum length approximately 20 spores per chain) on branched, almost verticillate aerial sporophores. The spores are ovoid, 0.6 to 0.8 micron by 1.0 to 1.4 micron, with a smooth surface.

Cell Wall Composition

Whole cell hydrolysates of this culture contain madurose (3-O-methyl-D-galactose) and the meso isomer of diaminopimelic acid (DAP). The culture also has a Type P-1 phospholipid pattern and no other diagnostic phospholipid other than some phosphatidyl glycerol. These characteristics are all very typical of members of the genus Actinomadura.

Amount of Growth

Good growth is observed in Bennett's agar. Gauze No. 2 agar, NZ-amine-starch-glucose agar (ATCC Medium 172), tomato paste-oatmeal agar, and yeast extract-malt extract agar; moderate growth is observed on Benedict's agar, Czapek's sucrose agar, glycerol-asparagine agar, Hickey-Tresner agar, and oatmeal agar; poor growth is observed on calcium malate agar, Gauze No. 1 agar, and inorganic salts-starch agar.

Vegetative Mycelium

On media where good growth occurred, the vegetative mycelium was observed to be raised and convoluted and was generally yellowish-gray shades in color.

Aerial Mycelium and Spore Color

Aerial mycelia and/or spore masses were white to 264. light gray in color. Aerial mycelia production is light on most media.

Soluble Pigments

Absent on many media; yellow pigment on Benedict's and glycerol-asparagine agars; yellow-green pigment on calcium malate agar; greenish brown pigment on NZ-amine-starch-gluclose agar; orange pigment on Bennett's and yeast extract-malt extract agars.

Physiological Reactions

No melanin pigments on peptone-iron agar and tyrosine agar (ISP-7); strong peptonization of litmus milk; strong proteolysis of nutrient gelatin; moderate reduction of nitrate; no hydrolysis of adenine or guanine; strong hydrolysis of hypoxanthine, tyrosine, and xanthine; weak hydrolysis of starch; hydrolysis of esculin; variable hydrolysis of urea. No growth at 4° C., 10° C., or 55° C.; moderate growth at 25° C., 28° C. and 45° C.; good growth at 32° C. and 37° C. Carbohydrate utilization as per the method of T. G. Pridham and D. Gottlieb, "The utilization of carbon compounds by some actinomycetales as an aid for species determination," J. Bacteriol. 56:107–114 (1948): good utilization of glucose, glycerol and trehalose; moderate utilization of maltose and sucrose; poor utilization of fructose, galactose, inositol, mannose, and melezitose; no utilization of adonitol, arabinose, dulcitol, lactose, mannitol, melibiose, raffinose, rhamnose, salicin, sorbitol and xylose. Acid production from carbohydrates by the method of Gordon, et al., supra: Good acid production from glucose, glycerol, maltose, sucrose and trehalose; weak acid production from galactose, inositol and mannose. Utilization of organic acids by the method of Gordon et al., supra: utilization of acetate, malate, propionate, pyruvate, succinate and tartrate; no utilization of benzoate, citrate, lactate, mucate and oxalate.

TABLE I

Cultural Characteristics of *Actinomadura yumaense* NRRL 12515
Incubation: 14 days   Temperature: 28° C.

| Medium | Amount of Growth | Aerial Mycelium and/or Spores | Soluble Pigment | Reverse Color |
|---|---|---|---|---|
| Benedict's Agar | Moderate to poor | Flat, powdery colonies; aerial mycelia white to 264. light gray | Yellowish | 89. pale yellow |
| Bennett's Agar | Good | No aerial mycelia; convoluted vegetative growth 93. yellowish gray to 80. grayish yellowish brown | Orange | 81. dark grayish yellowish brown |
| Calcium Malate Agar | Poor | Flat growth; sparse white aerial mycelia | Yellow-green | 90. greenish yellow |
| Czapek's Sucrose Agar | Poor to Moderate | Flat growth; moderate aerial mycelia vegetative growth 90. grayish yellow | None | 89. pale yellow |
| Gauze No. 1 Agar | Poor | Colorless flat growth; sparse white aerial mycelia | None | Colorless |
| Gauze No. 2 Agar | Good | Raised convoluted colonies; vegetative mycelia 93. yellowish gray; moderate aerial mycelia, 92. yellowish white | None | 72. dark orange yellow |
| Glycerol-Asparagine Agar | Poor to Moderate | Flat, powdery colonies; white aerial mycelia | Yellow | 89. pale yellow |
| Hickey-Tresner Agar | Moderate | Flat waxy colonies, 90. grayish yellow sparse aerial mycelia, white to 264. light gray | None | 90. grayish yellow |
| Inorganic Salts-Starch Agar | Poor | Flat, colorless, powdery colonies; white aerial mycelia | None | Colorless |
| NZ-amine-Starch-Glucose Agar | Good | Heavy convoluted growth, 61. grayish yellowish brown to 65. brownish black; moderate aerial mycelia, white to 264. light gray | Greenish brown | 78. dark yellowish brown |
| Oatmeal | Moderate | Flat waxy growth, 90. grayish | None | 90. grayish |

TABLE I-continued

Cultural Characteristics of *Actinomadura yumaense* NRRL 12515

Incubation: 14 days     Temperature: 28° C.

| Medium | Amount of Growth | Aerial Mycelium and/or Spores | Soluble Pigment | Reverse Color |
|---|---|---|---|---|
| Agar | | yellow; moderate aerial mycelia, white | | yellow |
| Tomato Paste Oatmeal Agar | Good | Flat waxy growth, 91. dark grayish yellow; trace of white aerial mycelia | None | — |
| Yeast Extract Malt Extract Agar | Good | Raised, waxy, convoluted colonies, 93. yellowish gray to 80. grayish yellowish brown; no aerial mycelia | Orange | 78. dark yellowish brown |

TABLE II

Micromorphology of *Actinomadura yumaense* NRRL 12515

| Medium | Aerial Mycelium and/or Sporiferous Structures | Spore Shape | Spore Size | Spore Surface |
|---|---|---|---|---|
| Czapek's Sucrose Agar | Aerial sporophores; branched, almost verticilate; carrying relatively short spiral chains of mature spores | ovid | 0.6–0.8 micron × 1.0–1.4 micron | Smooth |

TABLE III

Physiological Reactions of *Actinomadura yumaense* NRRL 12515

| Medium | Incubation Period | Amount of Growth | Physiological Reaction |
|---|---|---|---|
| Peptone-Iron Agar | 7 Days | Good | Slight browning |
| | 14 Days | Good | Slight browning |
| Tyrosine Agar | 7 Days | Moderate | No pigment |
| | 14 Days | Good | Yellowish pigment |
| Litmus Milk | 14 Days | Good | Good peptonization |
| | 28 Days | Good | Strong peptonization |
| Nutrient Gelatin | 14 Days | Good | Slight proteolysis |
| | 28 Days | Good | Total proteolysis |
| Nitrate Broth | 14 Days | Good | Very weak reduction |
| | 28 Days | Good | Moderate reduction |
| Adenine Agar | 14 Days | Good | No hydrolysis |
| | 21 Days | Good | No hydrolysis |
| Guanine Agar | 14 Days | Good | No hydrolysis |
| | 21 Days | Good | No hydrolysis |
| Hypoxanthine Agar | 14 Days | Good | Total hydrolysis |
| | 21 Days | Good | Total hydrolysis |
| Tyrosine Agar | 14 Days | Good | Strong hydrolysis |
| | 21 Days | Good | Strong hydrolysis |
| Xanthine Agar | 14 Days | Good | Moderate hydrolysis |
| | 21 Days | Good | Stong hydrolysis |
| NZ—amine with Soluble Starch and Glucose Agar (ATCC Med. No. 172) | 5 Days | Poor or no growth at 4° C., 10° C. and 55° C.; moderate growth at 25° C., 28° C. and 45° C.; good growth at 32° C. and 37° C. | |
| Urea Broth | 28 Days | Good | Decomposition variable |
| Esculin Broth | 14 Days | Good | Hydrolysis |
| | 28 Days | Good | Hydrolysis |
| Starch-Agar | 5 Days | Good | No Hydrolysis |
| | 10 Days | Good | No Hydrolysis |

TABLE IV

Carbon Source Utilization of *Actinomadura yumaense* NRRL 12515 on ISP-9 Carbohydrate Utilization Medium Incubation: 28 days     Temperature: 28° C.

| Carbon Source | Utilization |
|---|---|
| Adonitol | — |
| l-Arabinose | — |
| Dulcitol | — |
| Fructose | Poor |
| d-Galactose | Poor |

TABLE IV-continued

Carbon Source Utilization of *Actinomadura yumaense* NRRL 12515 on ISP-9 Carbohydrate Utilization Medium Incubation: 28 days     Temperature: 28° C.

| Carbon Source | Utilization |
|---|---|
| d-Glucose | Good |
| Glycerol | Good |
| i-Inositol | Poor |
| Lactose | — |
| Maltose | Fair |
| d-Mannitol | — |
| d-Mannose | Poor |
| d-Melezitose | Poor |
| d-Melibiose | — |
| d-Raffinose | — |
| l-Rhamnose | — |
| Salicin | — |
| Sorbitol | — |
| Sucrose | Fair |
| d-Trehalose | Good |
| d-Xylose | — |
| Negative Control | — |

TABLE V

Acid Production from Various Carbohydrates by *Actinomadura yumaense* NRRL 12515 on Gordon's Basal Inorganic Nitrogen Medium Incubation: 28 days     Temperature: 28° C.

| Carbon Source | Acid Production* 7 Days | 28 Days |
|---|---|---|
| Adonitol | — | — |
| l-Arabinose | — | — |
| Dulcitol | — | — |
| Fructose | — | — |
| d-Galactose | — | + |
| d-Glucose | +++ | +++ |
| Glycerol | ++ | +++ |
| i-Inositol | — | + |
| Lactose | — | — |
| Maltose | — | +++ |
| d-Mannitol | — | — |
| d-Mannose | — | + |
| d-Melezitose | — | — |
| d-Melibiose | — | — |
| d-Raffinose | — | — |
| l-Rhamnose | — | — |
| Salicin | — | — |
| Sorbitol | — | — |

TABLE V-continued

Acid Production from Various Carbohydrates
by *Actinomadura yumaense* NRRL 12515
on Gordon's Basal Inorganic Nitrogen Medium Incubation: 28 days     Temperature: 28° C.

| Carbon Source | Acid Production* | |
|---|---|---|
| | 7 Days | 28 Days |
| Sucrose | — | +++ |
| d-Trehalose | — | +++ |
| d-Xylose | — | — |
| Negative Control | — | — |

*+++ = Strong positive response
++ = Moderate positive response
+ = Slight positive response
— = Negative response

TABLE VI

Utilization of Organic Acids by *Actinomadura
yumaense* NRRL 12515 on Gordon's Modification
of Koser's Basal Agar (Koser's Citrate Agar)

Incubation: 28 days     Temperature: 28° C.

| Carbon Source | Utilization* |
|---|---|
| Acetate | + |
| Benzoate | — |
| Citrate | — |
| Lactate | — |
| Malate | + |
| Mucic Acid | — |
| Oxalate | — |
| Propionate | + |
| Pyruvate | + |
| Succinate | + |
| Tartrate | + |

*+ = Positive response
— = Negative response

It is to be understood that the term *Actinomadura yumaense* is not limited to strain *Actinomadura yumaense* NRRL 12515 or to strains fully answering the above growth and microscopic characteristics, which are given for illustrative purposes only. *Actinomadura yumaense* described herein includes all strains of *Actinomadura yumaense* which produce the antibiotic X-14868A and which cannot be definitely differentiated from *Actinomadura yumaense* NRRL 12515 and its subcultures, including mutants and variants thereof. The term "mutants" includes the natural (spontaneous) mutants of this organism as well as induced mutants produced from this organism by various mutagenic means known to those skilled in the art, such as exposure to x-ray radiation, ultraviolet radiation, nitrogen mustard, actinophages, nitrosamines, and the like. It is also desired and intended to include inter- and intraspecific genetic recombinants produced by genetic techniques known to those skilled in the art, such as for example conjunction, transduction and genetic engineering techniques.

Cultivation of *Actinomadura yumaense* may be carried out with a wide variety of solid or liquid culture media. Media which are useful for the production of antibiotic X-14868A include an assimilable source of carbon such as starch, sugar, molasses, glycerol, etc., an assimilable source of nitrogen such as protein, protein hydrolysate, polypeptides, amino acids, corn steep liquor, etc., and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is provided by forcing sterile air through or onto the surface of the fermenting medium. Further agitation in tanks is provided by a mechanical impeller. An antifoaming agent such as lard oil or silicone defoamer may be added as needed.

*Actinomadura yumaense* is grown and maintained on agar slants, for example Bennett's agar, Yeast Malt Agar, or ATCC Medium #172. ATCC Medium #172 is preferred. The slant is inoculated with a culture of *Actinomadura yumaense* and incubated at 28°–37° C., preferably at about 32° C., for approximately 7 days. These stock cultures may be maintained by serial transfers to fresh agar slants, or a plug of the agar containing mycelia from the well-grown agar slant may be used to inoculate liquid media.

Shake flask inoculations of *Actinomadura yumaense* are prepared by inoculating 100 ml. of sterile liquid medium in 500 ml. flasks with scrapings or washings of spores from an agar slant of the culture. Examples of suitable seed media are:

| Medium A | |
|---|---|
| Beef extract | 0.3% |
| Bacto ® tryptone[1] | 0.5% |
| Glucose | 1.0% |
| Yeast extract | 0.5% |
| Water qs | 100% |

[[1]A peptone, registered trademark of Difco Laboratories, Detroit, Michigan]

The pH is adjusted to 6.8–7.2 with dilute base, e.g. sodium hydroxide.

| Medium B | |
|---|---|
| Glucose | 1% |
| Starch | 2% |
| Yeast extract | 0.5% |
| N—Z Amine A ®[2] | 0.5% |
| Calcium carbonate | 0.1% |
| Water qs | 100% |

[[2]Casein digest, registered trademark of Sheffield Chemical Co.,Div. Nat'l. Dairy Products Corp., Norwich, N.Y.]

Medium B is preferred.

The flasks are incubated at a temperature of 25°–35° C., preferably at 32° C., and agitated vigorously on a rotary shaker for 1–4 days. This seed inoculum is then used to inoculate fermentation culture, or this culture may be frozen and stored to provide inoculum for subsequent seed cultures.

The following media are examples of those suitable for the fermentation of *Actinomadura yumaense* to produce antibiotic X-14868A:

| Medium C | |
|---|---|
| Glucose | 1.5% |
| Glycerol | 1.5% |
| Soy flour[3] | 1.5% |
| Calcium carbonate | 0.1% |
| Sodium chloride | 0.3% |
| Water qs | 100% |

| Medium D | |
|---|---|
| Glucose | 3% |
| Soy flour | 1.5% |
| Calcium carbonate | 0.1% |
| Sodium chloride | 0.3% |
| Water qs | 100% |

| Medium E | |
|---|---|
| Starch | 1% |
| Molasses | 2% |
| Soy flour | 1.5% |
| Calcium carbonate | 0.1% |
| Water qs | 100% |

-continued

| Medium F | |
|---|---|
| Glucose | 3% |
| Meat solubles | 2.5% |
| Sodium chloride | 0.2% |
| Calcium carbonate | 0.1% |
| Water        qs | 100% |

| Medium G | |
|---|---|
| Glucose | 3% |
| Soy flour | 0.5% |
| Ammonium sulfate | 0.3% |
| Sodium chloride | 0.2% |
| Calcium carbonate | 0.1% |
| Water        qs | 100% |

| Medium H | |
|---|---|
| Glucose | 3% |
| Ammonium sulfate | 0.3% |
| Dibasic potassium phosphate | 0.1% |
| Calcium carbonate | 0.2% |
| Sodium chloride | 0.1% |
| Water        qs | 100% |

[3May be substituted by cottonseed flour or meat solubles with equal effect.]

Medium D is preferred.

The fermentation may be carried out in 100 mls. of media in a 500-ml. flask inoculated with 3–10% (v/v) of a seed culture prepared as described above and incubated at 25°–35° C., preferably at about 32° C., for 24–72 hours with aeration. Samples of the fermentation culture may be frozen and stored for later use as inoculum for seed cultures.

Alternatively, the fermentation may be carried out in larger fermentation tanks equipped with aeration and agitation means. Each tank is inoculated with 3–10% (v/v) of inoculum prepared as described above. Aeration is supplied at the rate of 0.5 to 2.0 liter of sterile air per liter of broth per minute and the fermenting medium is agitated by an impeller driven at 200–400 rpm. The temperature is maintained at 25°–35° C., preferably at 32° C. The fermentation is continued until antibiotic accumulates in the fermentation medium, usually after 100–150 hours, at which time the antibiotic is harvested.

The antibiotic may be harvested and purified according to the methods described in U.S. Pat. No. 4,278,663, supra, or according to the following procedure:

The crude fermentation broth containing the whole cells, prepared as described above, is mixed with an equal volume of any non-hydrocarbon water-immiscible organic solvent. Methylene chloride or ethyl acetate is preferred. The organic phase is separated and concentrated in vacuo to an oily syrup.

The oily syrup is dissolved in methylene chloride and added to a column of silica gel, alumina, Sephadex LH-20 ® (Pharmacia Fine Chemicals Div. of Pharmacia. Inc., Piscataway, N.J.), or magnesium aluminum silicate. Examples of suitable solvents for developing the column are diethyl ether, ethyl acetate, a 1:1 to 1:7 (v/v) mixture of methylene chloride:ethyl ether, 10–40% acetone in methylene chloride, 2–10% lower alcohol (methanol is preferred) in methylene chloride, 2–15% acetonitrile in methylene chloride, or 2–15% dioxane in methylene chloride. Methylene chloride: ethyl acetate 1:1 (v/v) is preferred. Fractions are collected and checked for the presence of antibacterial activity by bioassay against a susceptible organism, e.g. *Bacillus subtilis*. Active fractions are combined and concentrated *in vacuo* to a residue. This residue is dissolved in an organic solvent, e.g. t-butanol (preferred), benzene, or p-dioxane, and freeze-dried.

The freeze-dried solid is dissolved in an appropriate organic solvent, e.g. methylene chloride, hexane, methylene chloride:ethyl acetate, diethyl ether, hexane:ethyl acetate, hexane:chloroform, or hexane:ether. Diethyl ether is preferred. This solution is shaken with water and the pH is adjusted to pH 1.5–4.0, preferably about 2.5, with any dilute mineral acid. The organic phase is separated, washed with water to remove any excess acid, dried over an appropriate drying agent, filtered, and concentrated to a residue in vacuo.

This residue is dissolved in an appropriate solvent and the solution is allowed to evaporate slowly, preferably at about 40° C. Examples of suitable solvents are methylene chloride, hexane, methylene chloride:ethyl acetate, diethyl ether, hexane:ethyl acetate, hexane:chloroform, or hexane:ether. Hexane:ether 5:2 (v/v) is preferred. The resulting crystals are collected and washed, preferably at about 4° C., with any moderately boiling hydrocarbon such as for example hexane or heptane, and air dried to yield as the final product the antibiotic X-14868A in the free acid form.

If the product is desired in the form of a salt, the free acid may be converted by treatment with the appropriate cation, preferably in the form of a dilute mineral base, according to procedures well-known to those skilled in the art.

The following Examples will serve to illustrate the invention without limiting it thereto. The Media A, B, C, etc. are those defined above. Unless otherwise specified, all procedures were performed at room temperature (approximately 22° C.) and at 1 atm pressure.

EXAMPLE 1

Washed spores from an agar slant of *Actinomadura yumaense* NRRL 12515 were used to inoculate a 500 ml. flask containing 100 ml. of sterile Medium B. The flask was incubated on a rotary shaker at 28° C. for 2 days.

A 5% inoculum of this culture was then transferred to 100 mls. sterile Medium C in a 500 ml. flask and incubated at 28° C. for 5 days on a rotary shaker.

The presence of antibiotic activity was monitored daily by bioassay against *Staphyylococcus aureus* ATCC 6538 P, *Bacillus subtilis*, and *Streptococcus faecalis*, and anthelmintic activity was monitored by bioassay against the free-living nematode *Caenorhabditis elegans*.

EXAMPLE 2

Seven 500 ml. flasks were prepared, each containing 100 mls. of one of the following sterile media:

Flask 1: 100 ml. Medium C
Flask 2: 100 ml. Medium C with 1.5% cottonseed flour substituted for the soy flour
Flask 3: 100 ml. Medium C with 1.5% meat solubles substituted for the soy flour
Flask 4: 100 ml. Medium D
Flask 5: 100 ml. Medium E
Flask 6: 100 ml. Medium F
Flask 7: 100 ml. Medium G These flasks were each inoculated with a 5% inoculum of *Actinomadura yumaense* NRRL 12515 grown in Medium B. The flasks were then incubated on a rotary shaker at 28° C. for four to six days.

Each of the above cultures was found to be active when assayed for antibiotic activity as in Example 1 and when assayed for anticoccidial activity against *Eimeria tenella* in chick kidney tissue cultures.

EXAMPLE 3

Frozen fermentation culture cells of *Actinomadura yumaense* NRRL 12515 were used to inoculate a 500 ml. flask containing 100 ml. sterile Medium B. The flask was then incubated at 32° C. for 4 days on a rotary shaker.

A 5% inoculum of this culture was then transferred to 100 ml. sterile Medium H in a 500 ml. flask and incubated at 28° C. for 5 days on a rotary shaker.

Antibacterial activity was confirmed as in Example 1 and anticoccidial activity as in Example 2.

The presence of antibiotic activity was also assayed by thin layer chromatography on silica gel plates developed in ethyl acetate:chloroform 70:30 (v/v). The presence of antibiotic X-14868A was confirmed by spraying with sulfuric acid and charring.

EXAMPLE 4

One hundred milliliters sterile Medium A in a 500 ml. flask was inoculated with washed spores from an agar slant of *Actinomadura yumaense* NRRL 12515. The flask was incubated at 32° C. for 2 days on a rotary shaker.

A 5% inoculum of this culture was then transferred to 100 ml. sterile Medium H in a 500 ml. flask and incubated on a rotary shaker at 32° C. for 2 days.

A 5% inoculum of this culture was then transferred to a 500 ml flask containing 100 ml. fresh sterile Medium H and incubated at 28° C. for 6 days on a rotary shaker.

Antibacterial activity was confirmed as in Example 1.

EXAMPLE 5

Two 500 ml. flasks each containing 100 ml. sterile Medium A were inoculated with a frozen seed culture of *Actinomadura yumaense* NRRL 12515 and incubated at 32° C. for 2 days on a rotary shaker.

The contents of the two flasks were then combined and added to 12 liters of fresh sterile Medium A in a 20 liter bottle. This culture was then incubated for 2 days at 28° C. with aeration.

The contents of this bottle were then transferred to a 300 liter seed tank containing 288 liters sterile Medium A and this culture was aerated and agitated for 25 hours at 32° C.

At the end of 25 hours' incubation, the 300 liters of seed culture were transferred to a 1500 liter fermentor containing 1200 liters of sterile Medium C. This culture was incubated with aeration and agitation for 115 hours at 28° C.

The fermentation broth was assayed for antibiotic activity by thin-layer chromatography on silica gel plates developed in ethyl acetate:chloroform 70:30 (v/v). The presence of antibiotic X-14868A was confirmed by spraying with sulfuric acid and charring. Alternatively, several of the developed plates were subjected to bioassay against *Bacillus subtilis* which showed the presence of antibiotic activity.

The presence of antibiotic X-14868A in the fermentation broth was also confirmed by reverse-phase high-pressure liquid chromatography.

EXAMPLE 6

A. A total of 1500 liters of fermentation broth, prepared as described in Example 5, was adjusted to pH 4 with 6 N HCl and mixed with equal volume of methylene chloride. The mixture was stirred for 2 hours; thereafter a methylene chloride layer settled to the bottom and was drawn off. This methylene chloride fraction was concentrated in vacuo to an oily syrupy material.

To this syrupy material was added 50 liters methanol and the mixture was filtered using diatomaceous earth as a filter aid. The filtrate was concentrated *in vacuo* to yield 1332 g. of residue.

This residue was then dissolved in 5 liters methylene chloride and added to a glass column 3 feet high and six inches in diameter packed with silica gel. The column was washed with 40 liters methylene chloride to remove the fatty material. The column was then developed with 30 liters methylene chloride:ethyl acetate 1:1 (v/v) and fractions of four liters each were collected. These fractions were assayed for antibacterial activity by bioassay against *Bacillus subtilis* Stansley R-78, grown on nutrient agar at pH 6.0. The fractions were also assayed by thin-layer chromatography on Polygram Sil G/UV254 ® [silica gel chromatographic substrate, Macherey and Nagel]. Samples of each fraction were loaded onto a thin-layer plate and chromatographed with chloroform: ethyl acetate 1:1 (v/v). The presence of antibiotic was detected by charring in the presence of sulfuric acid. Based on these two assays it was determined that fractions 1–6 contained antibiotic activity; these fractions were combined and concentrated in vacuo to a residue.

Trituration of this residue with 2 liters diethyl ether produced a suspension of crystals. These crystals were filtered off, washed with cold hexane, and air dried to yield 123 g. of crystalline antibiotic- X-14868A free acid hydrate.

B. The filtrate and washings from the last step above were combined and concentrated in vacuo to a syrup. Chromatography on Polygram Sil G/UV 254® as described above showed the presence of antibiotic activity. The syrup was chromatographed on a silica gel column as described in Part A above and the active fractions were collected, combined, and concentrated *in vacuo* to a residue.

This residue was dissolved in 1.5 liters diethyl ether and shaken with an equal volume of water. The pH was adjusted to 2.5 with 0.1 N HCl and the ether phase was separated and washed with three 500-ml. portions of water, then 500 ml. of water was added and the pH was adjusted to 10 with 0.1 N NaOH. The ether phase was again separated and washed with three 500-ml portions of water. Hexane (1.5 liters) was added to the ether phase and the mixture was concentrated in vacuo until the onset of crystallization; the mixture was then allowed to stand overnight at 4° C. The resulting crystals were collected and air dried to yield 121 g. of antibiotic X-14868A as the free acid hydrate.

C. The crystalline products of Steps A and B above were combined and dissolved in a mixture of 400 ml. methylene chloride in 2 liters of diethl ether and stirred with 3 g. Darco G-60 ® [decolorizing agent, Altas Chemical Ind., Wilmington, Del. ]. The solution was filtered to remove the decolorizing agent, and 1.5 liters hexane were added to the filtrate. This mixture was layered over 700 ml. water and 0.1 N HCl was added until the pH stabilized at 2.5 after shaking and settling. The aqueous layer was separated and discarded, and the organic layer was washed four times with 500 ml. portions of water. The washed organic layer was layered over 500 ml. water and 5 N NaOH was added until the pH stabilized at 10–11 after shaking and settling. The aqueous layer was separated and discarded and the organic layer was washed successively with three 500 ml. portions of water.

The washed organic layer was then dried over sodium sulfate and concentrated in vacuo to approximately 900 ml. The resulting suspension was warmed on a steam cone and then allowed to sit at about 40° C. overnight. The resulting crystals were collected on a funnel, washed with cold (4° C.) hexane, and air dried to yield a total of 218.7 g. antibiotic X-14868A free acid hydrate.

EXAMPLE 7

The fermentations of Examples 1-4 may be harvested and the harvest mash treated as in Example 6 to yield antibiotic X-14868A free acid hydrate.

We claim:

1. A process for preparing antibiotic X-14868A which comprises aerobically fermenting an antibiotic X-14868A-producing *Actinomadura yumaense* NRRL 125 15 or an antibiotic X-14868A-producing mutant thereof in a liquid medium containing assimilable sources of carbon, nitrogen, and inorganic salts, until substantial antibiotic activity is imparted to the fermentation broth and then recovering the antibiotic therefrom.

2. A process for preparing antibiotic X-14868A which comprises aerobically fermenting a liquid medium containing assimilable sources of carbon, nitrogen, and inorganic salts, which medium has been inoculated with a viable culture of an antibiotic X-14868A-producing *Actinomadura yumaense* NRRL 125 15 or an antibiotic X-14868A-producing mutant thereof, maintaining said fermentation culture at a temperature of 25°-35° C. for a period of 24-150 hours, harvesting the fermentation broth, and extracting the antibiotic therefrom.

3. A biologically pure culture of *Actinomadura yumaense* NRRL 125 15, said culture being capable of producing the antibiotic X-14868A in recoverable quantities upon fermentation in a liquid nutrient medium containing assimilable sources of carbon, nitrogen, and inorganic salts.

4. A biologically pure culture of the microorganism *Actinomadura yumaense* NRRL 125 15 according to claim 3, wherein said microorganism has spontaneously mutated such that the microorganism is genetically altered but still retains the ability to synthesize antibiotic X-14868A.

5. A biologically pure culture of the microorganism *Actinomadura yumaense* NRRL 125 15 according to claim 3, wherein said microorganism has been subjected to mutagenic means such that the microorganism is genetically altered but still retains the ability to synthesize antibiotic X-14868A.

* * * * *